United States Patent [19]

Garrett

[11] Patent Number: 5,347,655
[45] Date of Patent: Sep. 20, 1994

[54] EYEWEAR IN COMBINATION WITH A VISOR

[75] Inventor: L. A. Garrett, Columbia, S.C.
[73] Assignee: I-Sha-Vi, Inc., Columbia, S.C.
[21] Appl. No.: 89,255
[22] Filed: Jul. 9, 1993
[51] Int. Cl.⁵ .............................. A42B 1/24
[52] U.S. Cl. .............................. 2/10; 2/12; 2/453; 351/155
[58] Field of Search .......... 2/10, 12, 9, 453, 199; 351/155, 158

[56] References Cited

U.S. PATENT DOCUMENTS

| | | | |
|---|---|---|---|
| 2,648,091 | 8/1953 | Jones | 2/10 X |
| 4,117,553 | 10/1978 | Bay | 2/10 |
| 4,152,051 | 5/1979 | Van Tiem | 351/155 X |
| 4,527,291 | 7/1985 | Nussbickl | 2/453 X |
| 4,541,125 | 9/1985 | Phillips | 2/453 X |
| 4,819,274 | 4/1989 | Day | 2/10 |
| 4,916,754 | 4/1990 | Kang | 2/12 |

FOREIGN PATENT DOCUMENTS 0135356  4/1952  Sweden ........................ 2/10

Primary Examiner—Peter Nerbun
Attorney, Agent, or Firm—Michael A. Mann

[57] ABSTRACT

A sun visor with attached sunglasses rotatable incrementally between an up position, a down position and several intermediate positions. The frame of the sunglasses has a pair of posts extending laterally through holes in members dependent from the visor. The holes both have scalloped edges and the posts have a prismatic shape so that the scallops will engage the sides of the prismatic post and resist its rotation but not prevent rotation if sufficient force is applied to deform the scallops. The ends of the posts are conical and slotted to facilitate insertion of the posts through the holes in the dependent members and prevent removal because the diameter of the base of the cone is larger than the diameter of the hole.

9 Claims, 2 Drawing Sheets

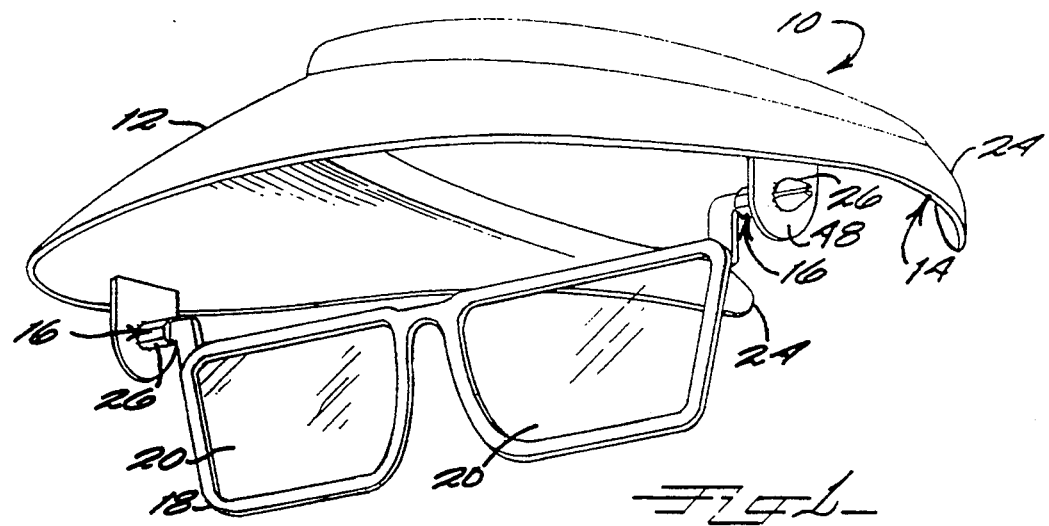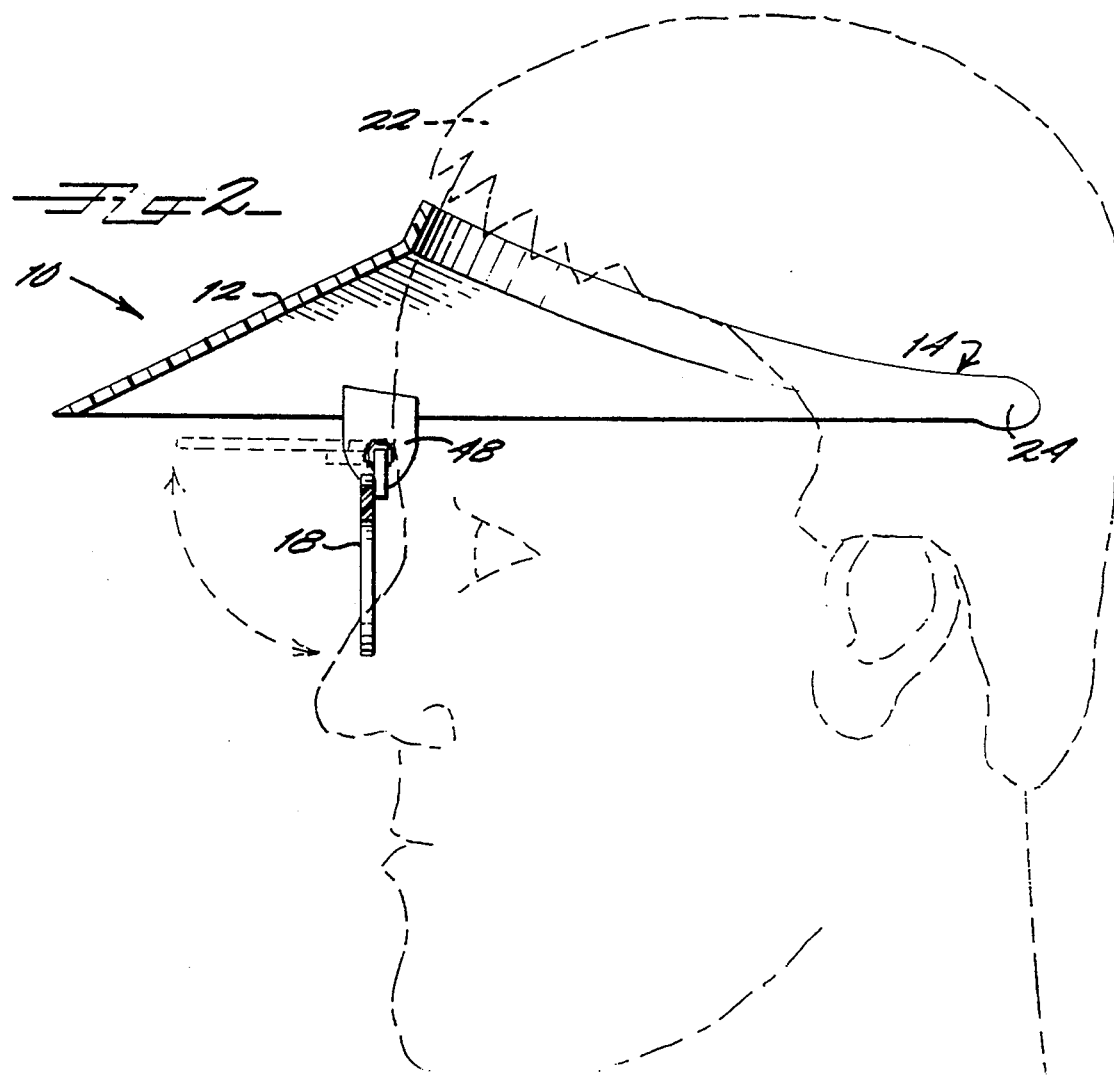

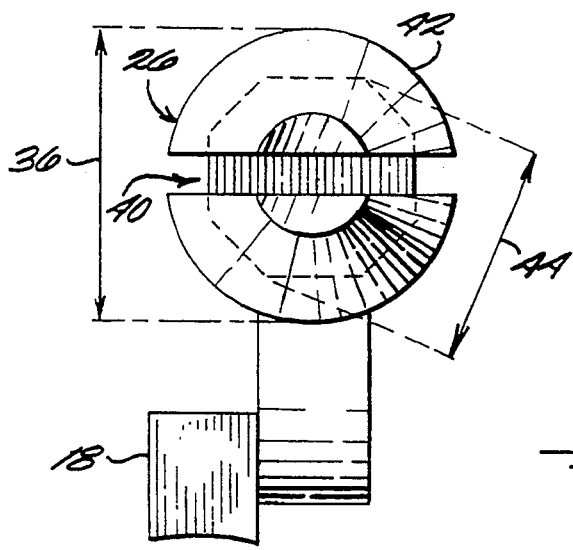
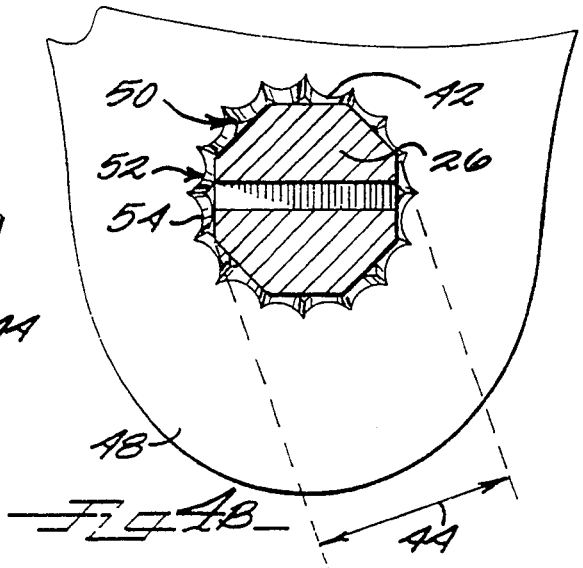
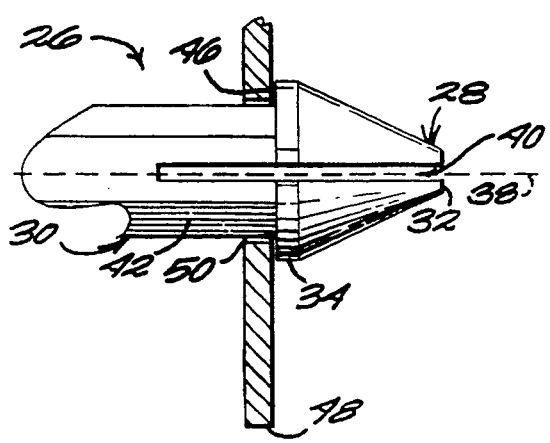
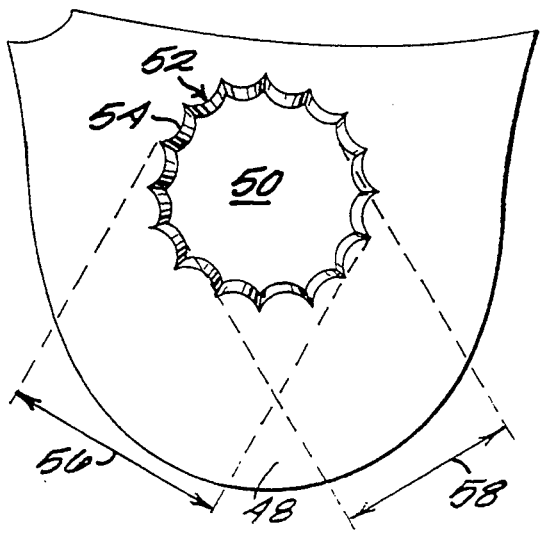
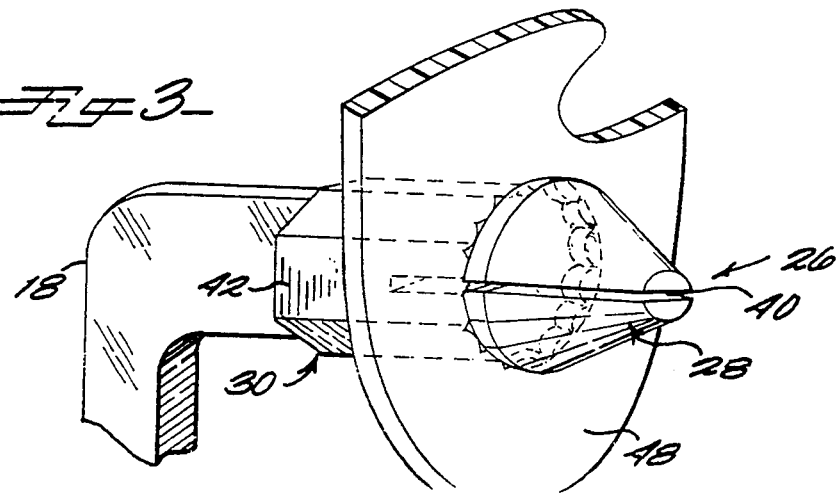

EYEWEAR IN COMBINATION WITH A VISOR

BACKGROUND OF THE INVENTION

1. Field of the Invention

The present invention relates to a device that combines a sun visor with eyewear. More particularly, the present invention relates to a sun visor with a lens having a frame, which can be incrementally rotated about its axis.

2. Discussion of Background

Our society thrives on outdoor activity. Those of us who enjoy the outdoors usually carry eyewear to protect against intense visible light and ultraviolet rays. Sunglasses, visors, or the combination of both have traditionally blocked dangerous ultraviolet sunlight while providing the user with a more comfortable perspective to better enjoy an outdoor activity.

Sunglasses are available in a multitude of styles and sizes but may not be suited for more active pursuits. Sun visors have many advantages: they are effective sun blocks, durable, inexpensive and often stylish for the consumer, and easy to manufacture. Sun visors, however, have limited shielding against reflecting sunlight, do not block ultraviolet light from the eyes and can be inadequate for glare off the surface of water or snow. Combining sunglasses with a sun visor is perhaps the best practical solution to enjoy the advantages of both worlds.

Sun visors that combine tinted lenses having a frame are well known. U.S. Pat. No. 2,638,593 granted to Eloranta and U.S. Pat. No. 4,815,838 granted to Liautaud attach the eyewear frame and a visor through slits formed in a visor that receive tabs notched on the side of the eyewear. U.S. Pat. No. 5,007,109 granted to Wheeler uses buckles that fit into snaps. U.S. Pat. No. 4,781,451 granted to McAllen uses eyeglass supports with VELCRO® patches that attach to headbands, caps and the like.

The rotation of a lens frame attached to a sun visor between an up and a down position is certainly advantageous for storing or giving alternate choices of protection for blocking more or less intense light. Combinations of visors with lenses having a frame that feature incremental rotation are well known. U.S. Pat. No. 1,696,198 granted to Gross and U.S. Pat. No. 5,105,475 granted to Lynd, et al. teach of incrementally rotating the eyeglasses on a visor or cap.

Although visors with eyewear exist, there remains a need for designs that permit incremental rotation of lenses from a stored, non-operational position to an operational position.

SUMMARY OF THE INVENTION

According to its major aspects and broadly stated, the present invention is an sun visor combined with a lens that has a frame, which can be incrementally rotated about an axis from a stored or "up" position against the visor to a "down" or operational position. The device is worn on a user's head to protect from sunlight. The device comprises a visor, means for holding the visor to the head, a frame, one or more lenses secured to the frame, and means for securing the frame to the visor. The visor is a typical visor in its preferred embodiment, that is, a member that extends from the forehead forward to shield the eyes from overhead sunlight and may slope slightly downward from the forehead. The visor is secured to the head by holding means such as a pair of arms that engage the sides of the head and are attached to the frame or a head-encircling strap or elastic band. The present visor has two spaced-apart, depending members each of which contains a hole dimensioned to receive part of the frame that will secure the frame to the visor. Each hole has a scalloped edge and is constructed of a resilient material.

Securing means comprise a pair of posts on opposing sides of the frame, each post having a first end and a second end. The first end passes through the holes in the depending member of the visor and is preferably conical in shape to facilitate insertion. The second end of the securing means is prismatic in shape, having a central axis and a prismatic diameter.

An important feature of the present invention is the combination of the scalloped edge of the hole in the depending member and the prismatic end of the post. The scalloped edge cooperates with the prismatic second end of the post of securing means by permitting rotation but biasing prismatic second end in certain positions so that incremental rotation of the frame is permitted simply and effectively.

The conical first end of the post is another feature of the present invention. The cone is preferably slit and the base of the cone defines a shoulder. The conical first end is easily pushed through the visor hole as the two halves of the cone, one on either side of the slit are pushed together by the force exerted on the cone by the edge of the hole in the visor, but once through the hole past the base of the cone, the shoulder prevents removal of the frame from the visor.

Other features and advantages will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a perspective drawing of the device according to a preferred embodiment of the present invention;

FIG. 2 is a cross sectional view of the device according to a preferred embodiment of the present invention;

FIG. 3 is a detailed view of securing means fixed to the visor according to the preferred embodiment of the present invention;

FIG. 4A is a cross sectional view of the first end of post according to the preferred embodiment of the present invention;

FIG. 4B is a side view of depending member showing hole having a scalloped according to the preferred embodiment of the present invention;

FIG. 5A is a side view of a post according to an alternative embodiment of the present invention; and FIG. 5B is a detailed view of dependent member with a scalloped edged hole according to a preferred embodiment of the present invention.

DETAILED DESCRIPTION OF A PREFERRED EMBODIMENT

The present invention is a device that combines eyewear with a visor adapted to be worn about the head. In the preferred embodiment, as generally shown in FIG. 1, a device 10, according to a preferred embodiment of the present invention, comprises a visor 12, means 14 for holding visor 12 to the head 22 of a user, a frame 18, a pair of lenses 20 secured to frame 18, and means 16 for securing frame 18 to visor 12.

Visor 12 is a generally arcuate cantilever, preferably formed from styrene-based composition by injection molding. Visor 12 rests against the brow of the user and extends outward and slightly downward so as to shield the eyes from direct sunlight overhead or in the foreground. Holding means 14 engages head 22 of the user to hold visor 12 in position. In the preferred embodiment shown in FIG. 1, holding means 14 comprises a pair of arms 24, but alternatively may embody a pair of interlocking straps, a continuous elastic band, or cap.

Securing means 16 is located on opposing sides of frame 18, and preferably integral therewith, for securing frame 18 to visor 12 in such a way that frame 18 can incrementally rotate from an up position, engaging visor 12, to a down position for use as shown in FIG. 2, or a number of positions therebetween, as seen best in FIG. 2. In any of these positions: up, down, or intermediate, the angle between visor 12 and frame 18 is not likely to change unless force is applied to frame 18.

Securing means 16 comprises a pair of posts 26 on each end of frame 18, directed laterally. Each post 26 has a first end 28 and a second end 30, as best seen in FIGS. 3, 4A, 5A and 5B. First end 28 is conical in shape, that is, first end 28 has a tip 32, a base 34, a diameter 36, and an axis 38 perpendicular to diameter 36 and extending through tip 32 and base 34. First end 28 of post 26 has a slot 40 formed therein, slot 40 beginning at tip 32 and extending along axis through base 34.

Second end 30 of post 26 is prismatic in shape. A prismatic shape is defined as a solid having parallel rectilineal figures with parallelograms as sides 42, each side 42 having a length. The prismatic shape is preferably equilateral and regular, that is the lengths of all sides 42 are the same and the angles between all sides are the same. Further, the prismatic shape has a prismatic diameter 44, and most preferably has six or eight sides 44 (as seen best in FIGS. 4A & 4 B). Diameter 36 at base 34 of first end 28 is greater than prismatic diameter 44 of second end 30 of post 26 thereby defining a shoulder 46 (FIG. 5).

Visor 12 has two spaced-apart, earlobe-like, depending members 48. Each member 48 contains a hole 50 that is dimensioned to receive one post 26. Each hole 50 of member 48 has an edge 52, which defines a series of scallops 54 (as best seen in FIG. 4B). A "scallop" is a convex or arcuate portion of edge 52; series of scallops 54 forms a number of continuous, arcuate portions as a radius from the center of hole 50 varies in length from shorter to longer as it sweeps through 360°. In the preferred embodiment, series of scallops 54 are beveled and form a generally polygonal shape having a plurality of curved sides, preferably, sixteen sides in the present embodiment when second end has eight sides. Edge 52 of hole 50 has a first hole diameter 58 that is the minimum diameter of hole 50 and a second diameter 56 that is the maximum diameter of hole 50. First hole diameter 58 should be smaller than prismatic diameter 44 but preferably less than second hole diameter 56.

Dependent member 48 is constructed of a resilient material such as plastic; frame may also be made of plastic but not necessarily a resilient plastic. First end 28 of post 26 is configured to fit through one hole 50 of each member 48. The resilient material of dependent member 48 deforms under the influence of the forces of first end 28 of post 26 being pushed through hole 50. When diameter 36 of base 34 of first end 28 is through hole 50 of member 48, shoulder thereafter impedes the removal of post 26.

Dependent member 48 grips second end 30 of post 26. The small gap between prismatic diameter 44 and second hole diameter 56 permits the rotation of frame 18 between up position and down position. Scalloped edge 52 resists rotation of post 26 when scalloped edge 52 engages sides 42 of post 26. As frame 18 is rotated, the force required to rotate alternately increases and then decreases as each side 42 of post 26 engages one scallop after another in series of scallops 52 so that post 26 will remain in one of "preferred" positions unless force is supplied to overcome the grip of scalloped edge 52 on second end 30. Frame 18 is rotated in a number of increments equaling the number of rectilinear sides 42 of second end 30 of post 26, preferably six or eight. Incremental rotation is important between a vertical position in front of the eyes of the user and a horizontal position away from the eyes of the user and against the innerside of visor 12 for adjusting the angle between visor 12 and frame 18 to suit the preference of the wearer and, in the up position, to store frame 18.

It will be apparent to those skilled in the art from a careful reading of the detailed description of the foregoing preferred embodiments that many modifications and substitutions can be made in the foregoing without departing from the spirit and scope of the invention. For example, it would be equivalent to have posts 26 as part of visor 12 and holes formed in frames 18 or to have either one large or two smaller lenses. The present invention is not limited to the specific example of uses given but, rather, is defined by the appended claims.

What is claimed is:

1. A device for wearing on a head of a user, comprising:
    a visor having two holes formed therein, each hole of said two holes defined by an edge with a series of scallops;
    means for holding said visor to said head;
    a frame;
    a lens secured to said frame;
    means for securing said frame to said visor so that said frame has an up position against said visor and a down position away from said visor, said frame being rotatable between said up and said down positions, said securing means having two posts, each post of said two posts having a first end and a second end, said first end of said each post having a conical shape to penetrate into one hole of said two holes, said second end of said each post having a prismatic shape for rotatably engaging said edge of one hole of said two holes, said series of scallops of said each hole permitting incremental rotation of said post.

2. The device as recited in claim 1, wherein said holding means further comprises a pair of arms, said pair of arms that engage said head of said user to hold said visor.

3. A device for use on a head of a user, comprising:
    a visor having two holes formed therein, each hole of said two holes defined by an edge with a series of scallops;
    means for holding said visor to said head;
    a frame;
    a lens secured to said frame; and
    means for securing said frame to said visor so that said frame has an up position against said visor and a down position away from said visor, said frame being rotatable between said up and said down positions through at least one intermediate position, wherein said visor has means formed therein for resisting rotation of said frame from said up position, said down position and said intermediate position, said securing means having two posts, each post of said two posts having a first end and a second end, said first end of said each post having a conical shape to penetrate into one hole of said two holes, said second end of said each post having a prismatic shape for rotatably engaging said edge of one hole of said two holes, said series of scallops of said each hole permitting incremental rotation of said post.

4. The device as recited in claim 3, wherein said first end of said each post has a conical shape with a tip, a base, a diameter, an axis extending through said tip and said base, and a slot formed therein to penetrate into said one hole of said two holes.

5. The device as recited in claim 3, wherein said holding means further comprises a pair of arms to engage said head of said user.

6. The device as recited in claim 3, wherein said visor has two dependent members made of a resilient material and each having a hole defined by an edge with a series of scallops, and wherein said each post has a conical shape with a tip, a base, a diameter, and an axis perpendicular to said diameter and extending through said tip and said base, said first end having a slot formed therein, said first end of said post configured to penetrate into said each hole in said dependent member.

7. The device as recited in claim 3, wherein said edge of said each hole is dimensioned to engage said second end and to resist rotational of said second end of said post, said series of scallops deforming when said second end of said post is rotated.

8. A device for use on a head of a user, comprising:

a visor having two dependent members, each dependent member made of a resilient material and having a hole formed therein, each hole having a hole diameter and a scalloped edge;

means for holding said visor to said head;

a frame;

a lens secured to said frame; and two posts attached to said frame and inserted in said holes of said dependent members and rotatable therein so that said frame can rotate between an up position against said visor and a down position away from said visor and through at least one intermediate position, said holes and said posts formed to resist rotation from said up position, said down position and said at least one intermediate positions, each post having a first end and a second end, said first end having a conical shape with a tip, a base having a base diameter, an axis perpendicular to said base diameter and extending through said tip and said base, and a slot formed therein, said second end having a prismatic shape having a prismatic diameter, said diameter of said base of said first end being greater than said prismatic diameter and said hole diameter, said scalloped edge engaging said second end and resisting rotation of said post but deforming when said second end of said post is rotated.

9. The device as recited in claim 8, wherein said hole has a diameter and each post has a conical shape with a maximum diameter and a slot formed therein, said maximum diameter of said conical shape being larger than said diameter of said hole so that when said each post is inserted through said hole, said conical shape facilitates insertion and said slot closes so that said conical shape can pass through said hole.

* * * * *